(12) United States Patent
Long et al.

(10) Patent No.: US 11,141,327 B2
(45) Date of Patent: Oct. 12, 2021

(54) SYSTEM FOR INTERVENING AND IMPROVING THE EXPERIENCE OF THE JOURNEY OF AN ABSORBENT ARTICLE CHANGE

(71) Applicant: Kimberly-Clark Worldwide, Inc., Neenah, WI (US)

(72) Inventors: Andrew M. Long, Neenah, WI (US); Jonathan D. Boulos, Neenah, WI (US); Joseph P. Fell, Kaukauna, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/771,849

(22) PCT Filed: Dec. 18, 2018

(86) PCT No.: PCT/US2018/066172
§ 371 (c)(1),
(2) Date: Jun. 11, 2020

(87) PCT Pub. No.: WO2019/126131
PCT Pub. Date: Jun. 27, 2019

(65) Prior Publication Data
US 2021/0007914 A1    Jan. 14, 2021

Related U.S. Application Data

(60) Provisional application No. 62/608,165, filed on Dec. 20, 2017.

(51) Int. Cl.
*A61F 13/84* (2006.01)
*A61M 21/02* (2006.01)
(Continued)

(52) U.S. Cl.
CPC ............. *A61F 13/84* (2013.01); *A61M 21/02* (2013.01); *A61F 2013/424* (2013.01);
(Continued)

(58) Field of Classification Search
CPC .................. A61M 21/00; A61M 21/02; A61M 2021/0016; A61M 2021/0027;
(Continued)

(56) References Cited

U.S. PATENT DOCUMENTS

D485,461 S    1/2004  Sams et al.
D540,501 S    4/2007  Wang
(Continued)

FOREIGN PATENT DOCUMENTS

CN    2313564 Y    4/1999
CN    202208487 U  5/2012
(Continued)

OTHER PUBLICATIONS

Nooralahiyan, A.Y. et al., "Vehicle classification by acoustic signature", Mathematical and Computer Modelling, vol. 27, Issues 9-11, May-Jun. 1998, pp. 205-214.
(Continued)

*Primary Examiner* — Carrie R Dorna
(74) *Attorney, Agent, or Firm* — Kimberly-Clark Worldwide, Inc.

(57) ABSTRACT

A system for intervening in an absorbent article change process by a user to improve the experience of the absorbent article change process is disclosed. The system can include a memory device, an auditory capture mechanism, and a processor. The memory device can be configured to store an absorbent article acoustic signature model. The absorbent article acoustic signature model can be indicative of a potential change of the absorbent article. The processor can be configured to analyze a captured potential use sound (Continued)

profile in relation to the absorbent article acoustic signature model and to interpret the first qualifying match in view of at least one environmental input. The system can be configured to selectively generate a first output based on the first qualifying match and the at least one environmental input. The first output can be recognizable by the user through visual, audible, or olfactory senses.

20 Claims, 6 Drawing Sheets

(51) Int. Cl.
*A61F 13/42* (2006.01)
*A61M 21/00* (2006.01)

(52) U.S. Cl.
CPC .............. *A61F 2013/8482* (2013.01); *A61M 2021/0016* (2013.01); *A61M 2021/0027* (2013.01); *A61M 2021/0044* (2013.01)

(58) Field of Classification Search
CPC ..... A61M 2021/0044; A61M 2021/005; A61F 13/84; A61F 2013/242; A61F 2013/8476; A61F 2013/8479; A61F 2013/8482
See application file for complete search history.

(56) References Cited

U.S. PATENT DOCUMENTS

| | | | |
|---|---|---|---|
| D564,169 S | 3/2008 | Wang | |
| 7,700,821 B2 | 4/2010 | Ales, III et al. | |
| 8,274,393 B2 | 9/2012 | Ales et al. | |
| 8,775,013 B1 | 7/2014 | Smailus | |
| 8,973,444 B2 | 3/2015 | Hill et al. | |
| D737,013 S | 8/2015 | Beumer | |
| D747,061 S | 1/2016 | Valderrama et al. | |
| 9,289,090 B2 | 3/2016 | Yuan et al. | |
| 9,470,776 B2 | 10/2016 | Chan et al. | |
| D775,447 S | 12/2016 | Stravitz | |
| 9,591,721 B2 | 3/2017 | Nolan et al. | |
| 2003/0206109 A1 | 11/2003 | Yang | |
| 2007/0047568 A1 | 3/2007 | Wang et al. | |
| 2007/0194893 A1 | 8/2007 | Deyoe | |
| 2008/0214949 A1 | 9/2008 | Stivoric et al. | |
| 2008/0266122 A1 | 10/2008 | Ales et al. | |
| 2012/0220969 A1 | 8/2012 | Jang et al. | |
| 2013/0076509 A1 | 3/2013 | Ahn | |
| 2013/0123654 A1 | 5/2013 | Rahamim et al. | |
| 2014/0032268 A1 | 1/2014 | Kruglick et al. | |
| 2015/0087935 A1 | 3/2015 | Davis et al. | |
| 2015/0157512 A1 | 6/2015 | Abir | |
| 2015/0316512 A1 | 11/2015 | Nicq | |
| 2015/0379463 A1 | 12/2015 | Sarangi | |
| 2016/0017905 A1 | 1/2016 | Cascolan et al. | |
| 2016/0125759 A1 | 5/2016 | Dougherty et al. | |
| 2016/0334771 A1 | 11/2016 | Laulagnet et al. | |
| 2017/0186124 A1 | 6/2017 | Jones et al. | |
| 2017/0193825 A1 | 7/2017 | Schlechter et al. | |
| 2017/0205783 A1 | 7/2017 | Tannenbaum et al. | |
| 2017/0206273 A1 | 7/2017 | Tannenbaum et al. | |
| 2017/0252225 A1 | 9/2017 | Arizti et al. | |
| 2017/0354547 A1 | 12/2017 | Abir | |

FOREIGN PATENT DOCUMENTS

| | | | |
|---|---|---|---|
| CN | 203216600 U | 9/2013 | |
| CN | 103989557 A | 8/2014 | |
| CN | 204624438 U | 9/2015 | |
| CN | 204776976 U | 11/2015 | |
| CN | 105752557 A | 7/2016 | |
| CN | 105947488 A | 9/2016 | |
| CN | 106429085 A | 2/2017 | |
| CN | 106429114 A | 2/2017 | |
| CN | 107133698 A | 9/2017 | |
| CN | 206480052 U | 9/2017 | |
| EP | 1091773 B1 | 2/2007 | |
| IN | 201621038041 A | 12/2016 | |
| IN | 201721011276 A | 9/2017 | |
| JP | 2003141256 A | 5/2003 | |
| KR | 20110111194 A | 10/2011 | |
| KR | 20160038573 A | 4/2016 | |
| KR | 20160133588 A | 11/2016 | |
| KR | 101705278 B1 | 2/2017 | |
| KR | 101731207 B1 | 4/2017 | |
| TW | M515376 U | 1/2016 | |
| WO | 02080831 A1 | 10/2002 | |
| WO | 16161483 A1 | 10/2016 | |
| WO | 17066513 A1 | 4/2017 | |
| WO | 17074406 A1 | 5/2017 | |

OTHER PUBLICATIONS

Sharma, Pradmod et al., "Diagnosis of Motor Faults Using Sound Signature Analysis", International Journal of Innovative Research in Electrinics, Instrumentation and Control Engineering, vol. 3, Issue 5, May 2015.

Brandtrust, "Diaper Journey and the Value of Mom Connection", Section 04 The Diaper Journey.

Nooralahiyan, Amir Y et al., "A field trial of acoustic signature analysis for vehicle classification", Researchgate, Aug. 1997, https://www.researchgate.net/publication/223533971_A_field_trial_of_acoustic_signature_analysis_for_vehicle_classitication.

Kakar, Varun Kumar et al., "Techniques of Acoustic Feature Extraction for Detection and Classification of Ground Vehicles", International Journal of Emerging Technology and Advanced Engineering, Feb. 2013, http://www.ijetae.com/files/Volume3Issue2/IJETAE_0213_70.pdf.

Li, Weidong et al., "Detection of Induction Motor Faults: A Comparison of Stator Current", Vibration and Acoustic Methods Journal of Vibration and Control, 1, Aug. 2004, http://citeseerx.ist.psu.edu/viewdoc/download?doi=10.1.1.913.3017&rep=rep1&type=pdf.

Wang, James M., "An Internet Based System to Monitor Aircraft's Health", MIT, Jun. 1, 2001, pp. 12, 13, 25, https://dspace.mit.edu/bitstream/handle/1721.1191731/48271993-MIT.pdf?sequence=2.

Mamun et al.,"Real time solid waste bin monitoring system framework using wireless sensor network", Institute of Electrical and Electronics Engineers Inc., Jan. 15-18, 2014, https://www.researchgate.net/profile/MA_Hannan/publication/286593286_Real_time_solid_waste_bin_monitoring_system_framework_using_wireless_sensor_network/links/569477e508ae425c68964691.pdf.

Vicentini, F. et al., "Sensorized waste collection container for content estimation and collection optimization", Waste Management, May 2009, https://www.ncbi.nlm.nih.gov/pubmed/19103480.

Wen, Ming-Hui, "Goo9: A wireless sensor network system for wet diaper detection", International Conference on Applied System Innovation (ICASI), May 2017, https://www.researchgate.net/publication/318694628_Goo_A_wireless_sensor_network_system_for_wet_diaper_detection.

Taichun, Qin et al., "Design of GSM-Based Tele-monitoring and Alarm System for Disposable Diaper", Green Computing and Communications, Aug. 2013, https://www.researchgate.net/publication/261229615_Design_of_GSM-Based_Tele-monitoring_and_Alarm_System_for_Disposable_Diaper.

Co-pending U.S. Appl. No. 16/771,830, filed Jun. 11, 2020, by Long et al. for "System for Documenting Product Usage by Recognizing an Acoustic Signature of a Product".

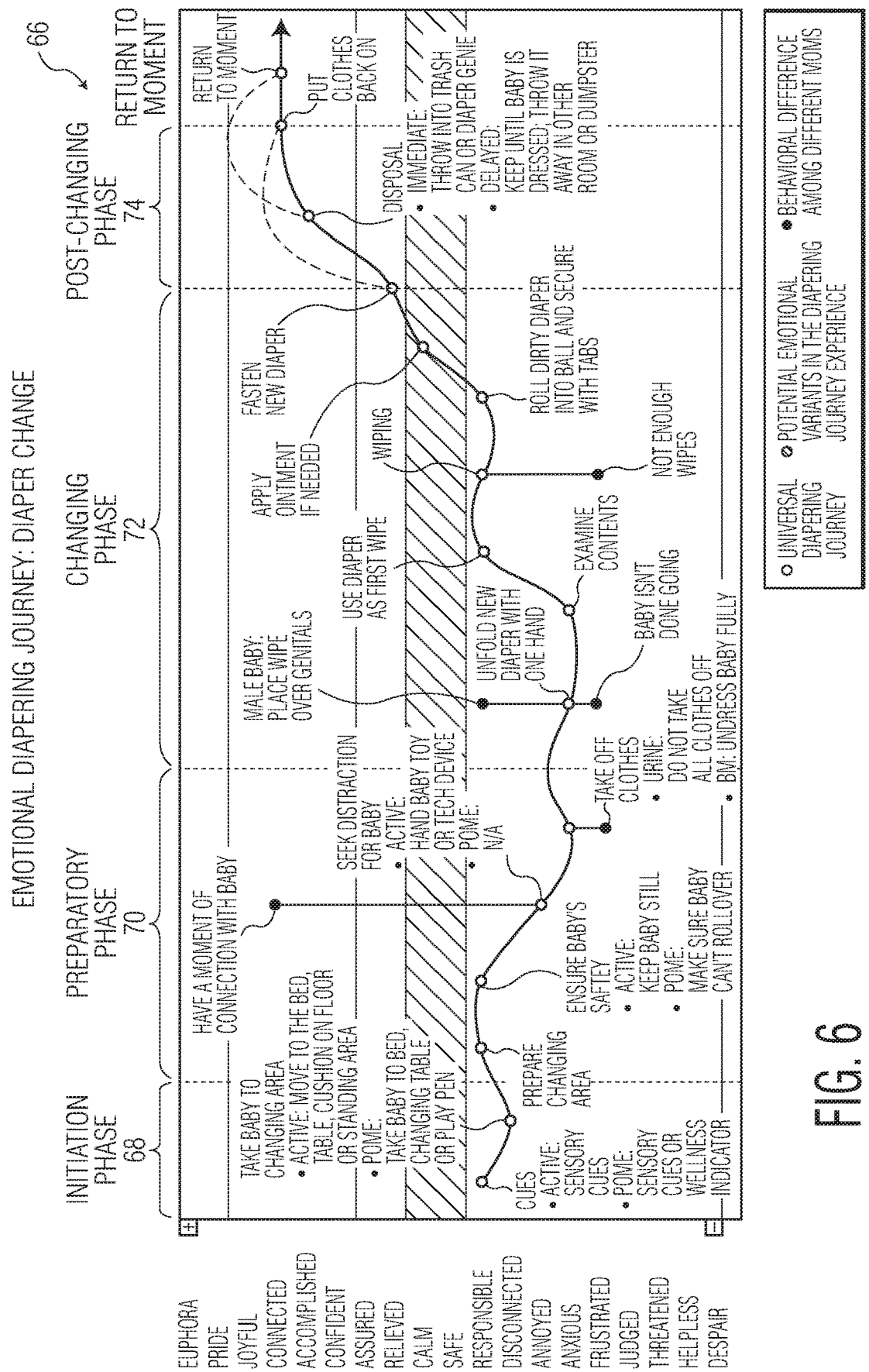

SYSTEM FOR INTERVENING AND IMPROVING THE EXPERIENCE OF THE JOURNEY OF AN ABSORBENT ARTICLE CHANGE

TECHNICAL FIELD

The present disclosure relates to systems for intervening and improving the experience of a consumable product. More specifically, the present disclosure relates to systems for intervening and improving the experience of the journey of an absorbent article change.

BACKGROUND OF THE DISCLOSURE

In the life of a caregiver, necessary changes in absorbent articles occur frequently. Absorbent articles may need to be changed at various points in the day, or even at various points at night. The act of changing an absorbent article by a caregiver can disrupt the flow and momentum of the daily activities of the caregiver as changes can come about unpredictably. Each change of an absorbent article causes the caregiver to pause from their current activities, possibly interrupting key moments or the flow of the day. The changing of an absorbent article can also create a threat for associated behavioral or mood changes of the wearer of the absorbent article. As such, from the moment a caregiver realizes or is informed there may be a need to change an absorbent article until the absorbent article is fully changed and the caregiver resumes their prior activity, a journey including various emotions may occur for both the caregiver and the wearer of the absorbent article. Some of these emotions may affect the enjoyment of the caretaker's or wearer's following activities after the change.

Various existing equipment and media for trying to improve upon the experience the caregiver and the wearer of the absorbent article often require manual manipulation to start or stop, which may be inconvenient, inaccessible, and non-hygienic based on the mood of the wearer and the particular circumstances of the absorbent article change. Automated sensors that do exist, such as simple motion or noise detection sensors, cannot capture various environmental inputs of a changing situation, such as the emotional range of a caregiver or wearer of the absorbent article, during the journey of an absorbent article change.

Accordingly, there is a desire for systems that allow for more convenient intervention during the journal of an absorbent article change and that enhance the experience of the change for the caregiver and/or the wearer.

SUMMARY OF THE DISCLOSURE

In one embodiment, a system is disclosed. The system can include a memory device configured to store an absorbent article acoustic signature model. The absorbent article acoustic signature model can be indicative of a potential change of the absorbent article and can be emitted from the absorbent article during use of the absorbent article. The system can also include an auditory capture mechanism configured to monitor an absorbent article change environment for a potential use sound profile and to capture the potential use sound profile while the product is being used. The system can additionally include a processor in electrical communication with the auditory capture mechanism. The processor can be configured to analyze the captured potential use sound profile in relation to the absorbent article acoustic signature model. The processor can be further configured to signal a first qualifying match when the captured potential use sound profile meets the absorbent article acoustic signature model. The processor can be further configured to interpret the first qualifying match in view of at least one environmental input. The at least one environmental input can be selected from the group consisting of: time of day, attitude recognition of a wearer of the absorbent article, and attitude recognition of a user of the absorbent article. The system can be configured to selectively generate a first output based on the first qualifying match and the at least one environmental input. The first output can be recognizable by a user through visual, audible, or olfactory senses.

In another embodiment, a system for intervening in an absorbent article change process by a user is disclosed. The absorbent article change process can include an initiation phase, a preparatory phase, a changing phase, and a post-changing phase. The system can include a memory device configured to store at least one preparatory phase auditory cue acoustic model. The at least one preparatory phase auditory cue acoustic model can be representative of an acoustic profile of the preparatory phase. The system can also include an auditory capture mechanism configured to monitor an absorbent article change environment for potential preparatory phase auditory cue sound profiles and to capture potential preparatory phase auditory cue sound profiles. The system can further include a processor in electrical communication with the auditory capture mechanism. The processor can be configured to analyze a captured potential preparatory phase cue sound profile in relation to the at least one stored preparatory phase auditory cue acoustic model. The processor can be further configured to signal a first qualifying match when the captured potential preparatory phase cue sound profile meets the at least one stored preparatory phase auditory cue acoustic model. The processor can be further configured to interpret the first qualifying match in view of at least one environmental input. The system can be configured to selectively generate a first output based on the first qualifying match and the at least one environmental input. The first output can be recognizable by the user through visual, audible, or olfactory senses.

In yet another embodiment, a computer program product is disclosed. The computer program product can include code embodied on a non-transitory computer-readable medium and can be configured to be executed on one or more processors. The computer program product can be configured to perform the operation of storing an absorbent article acoustic model. The absorbent article acoustic signature model can be indicative of a potential change of the absorbent article and can be emitted from the absorbent article during use of the absorbent article. The computer program product can also be configured to perform the operation of monitoring an absorbent article change environment for a potential use sound profile and capturing the potential use sound profile with an auditory capture mechanism. The computer program product can be further configured to perform the operation of analyzing the captured potential use sound profile in relation to the stored absorbent article acoustic signature model. The computer program product can be configured to perform the operation of signaling a first qualifying match when the captured potential use sound profile meets the stored absorbent article acoustic signature model. Additionally, the computer program product can be configured to perform the operation of interpreting the first qualifying match in view of at least one environmental input. The at least one environmental input can be selected from the group consisting of: time of day, attitude recognition of a wearer of the absorbent article, and attitude recognition of a user of the absorbent article. Furthermore, the computer program product can be configured to perform the operation of and selectively generating a first output based on the first qualifying match and the at least one environmental input. The first output can be recognizable by the user through visual, audible, or olfactory senses.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 6 is a plot of an exemplary diapering journey.

Figure 1:
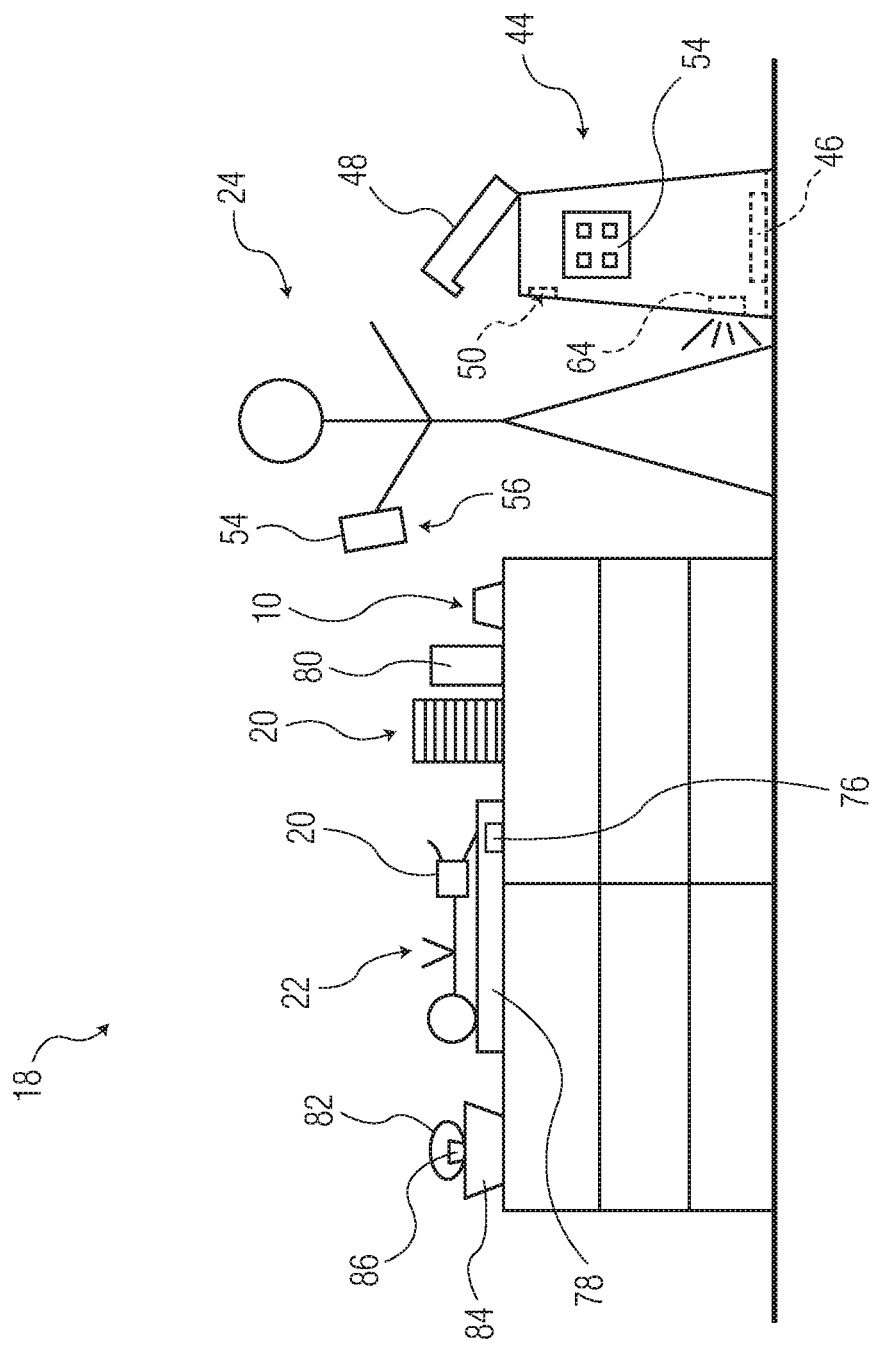
FIG. 1 is a front plan view of an absorbent article change environment.

Repeat use of reference characters in the present specification and drawings is intended to represent the same or analogous features or elements of the disclosure.

DETAILED DESCRIPTION OF THE DISCLOSURE

Figure 2:
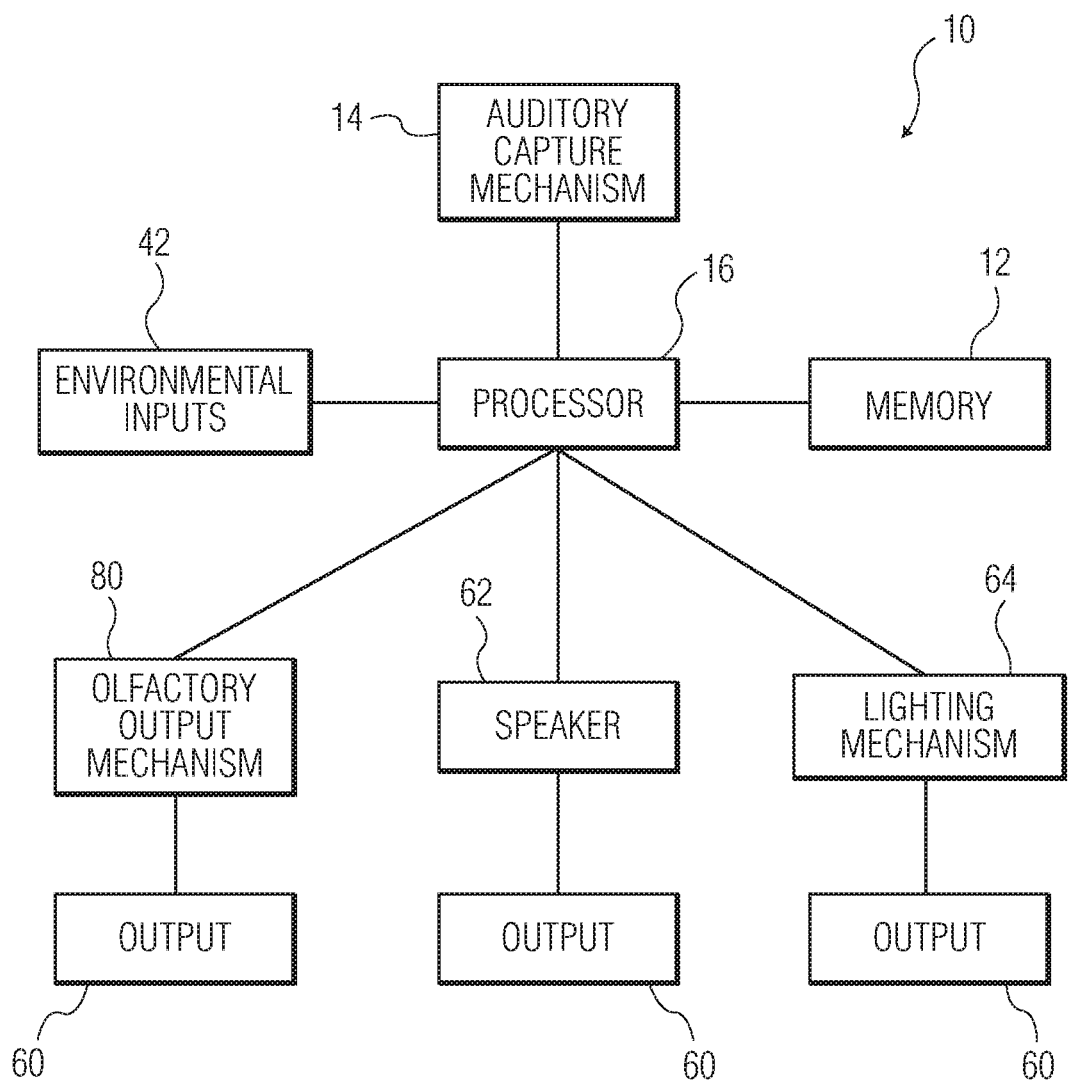
FIG. 2 is a schematic diagram of a system for intervening and improving the experience of a product change.

In an embodiment, the present disclosure is generally directed towards systems 10, such as that illustrated in FIGS. 1 and 2, for intervening in an absorbent article 20 change. Such systems 10 can include equipment that can be configured to capture and recognize auditory cues that are representative of various phases of an absorbent article 20 change. Such systems 10 can also be configured to selectively generate one or more outputs based on recognizing one or more auditory cues and at least one environmental input to intervene and to improve the experience of an absorbent article 20 change. In one aspect of the disclosure, a computer program product can include code embodied on a non-transitory computer-readable medium for performing the actions described herein for the system 10.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. As used herein, the terminology of "first," "second," "third", etc. does not designate a specified order, but is used as a means to differentiate between different occurrences when referring to various features in the present disclosure. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "electronically connected" or "in electrical communication" means that a component is configured to electronically communicate with another component through the same circuit, connected by wire, infrared (IR), radio frequency (RF), Bluetooth, wifi, cellular, or any other suitable connection means.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "user" refers herein to one who uses the system. In the context of a product of an absorbent article, a "user" can be a caregiver who fits the absorbent article, such as, but not limited to, a diaper, diaper pant, training pant, youth pant, incontinent product, or other absorbent article about the wearer of one of these absorbent articles. A user and a wearer can be one and the same person in some situations.

FIGS. 1-6 describe one exemplary embodiment of a system 10 for intervening in an absorbent article 20 change. One example of an absorbent article 20 shown and described herein is a diaper, however, the system 10 as described herein is not limited to changes of only diapers, and can be utilized for other absorbent articles, including, but not limited to: diaper pants, training pants, youth pants, swim pants, feminine hygiene products, including, but not limited to, menstrual pads or pants, incontinence products, medical garments, surgical pads and bandages, other personal care or health care garments, and the like.

In one exemplary embodiment, a system 10 can include a memory device 12, an auditory capture mechanism 14, and a processor 16. The components of the system 10 can be configured to be on a single device, or can be located on more than one device and be configured to be electronically connected with one another. In some embodiments, it is contemplated that one or more components of the system 10 can be configured to be resident on or communicate with a device that performs other functions system 10, such as a smart speaker device, for example, a GOOGLE HOME device or an AMAZON ECHO device. Alternatively or additionally, the system 10 can be configured to be resident on or communicate with other devices, including, but not limited to, smartphones, wearable smart devices (e.g., watches), smart TVs, remote controls, cars, computers, and tablets.

As portrayed in FIG. 1, the system 10 can be utilized in at least one absorbent article change environment 18. The absorbent article change environment 18 may vary depending on which type of absorbent article(s) 20 the system 10 is configured for, as well as even the particular habits of each user. For example, FIG. 1 displays that the system 10 can be configured for use in an absorbent article change environment 18 that is a changing area for an absorbent article 20 worn by a wearer 22 and changed by a user 24, such as a parent. Such an absorbent article change environment 18 may be a portion of a room of a house, an entire room, a hallway, or other area where the absorbent article 20 is frequently changed. In some embodiments, the system 10 can be configured to have more than one auditory capture mechanism 14 such that more than one absorbent article change environment 18 can be monitored simultaneously and without having to move any auditory capture mechanisms 14. In some embodiments, the system 10 can be configured such that it is used on or as part of a device that a user 24 typically carries with himself/herself (such as a smartphone), and as such, can monitor any environment that the user 24 finds himself/herself in which an absorbent article 20 may need to be changed.

The memory system 12 can be configured to store one or more acoustic models. An acoustic model, as used herein, means data, of various forms, that can be representative of an acoustic profile of an absorbent article 20 emitted during use of the absorbent article 20 or representative of an acoustic profile of an auditory phase cue for one or more phases in the absorbent article 20 change process. Examples of various forms of acoustic models can include, but are not limited to: a sound profile that is documented in terms of amplitude versus time, frequency profile (frequency versus time), a sound pressure profile, and a trained model 41 that can be analyzed with neural network analysis (as discussed further below). The memory system 12 can be configured to store one or more acoustic models for one or more different sizes and/or types of absorbent articles 20, which may or may not be related. The memory system 12 can be configured to store these one or more acoustic model(s) in a database. Such a database can be stored on either a hard drive or on one or more servers accessible remotely through a network, such as a public or private local area network, a local or wide area private intranet, or a wide area public interwork network such as the Internet. Such a database can be stored on either a hard drive, solid-state memory, or on one or more servers accessible remotely through a network, such as a public or private local area network, a local or wide area private intranet, or a wide area public interwork network such as the Internet. Alternatively or additionally, the memory system 12 can be configured to store the one or more acoustic signature models of product(s) within an integrated circuit or field-programmable gate array (FPGA).

In one embodiment, an acoustic signature model can be representative of an acoustic profile that is emitted by a fastening system 30 (as labeled in FIG. 3) of an absorbent article 20 being disengaged from a fastened condition, such as when the absorbent article 20 is in the process of being changed. Such an acoustic signature model can correlate to the absorbent article 20 being changed as part of the changing process 66 of the absorbent article 20.

Figure 3:
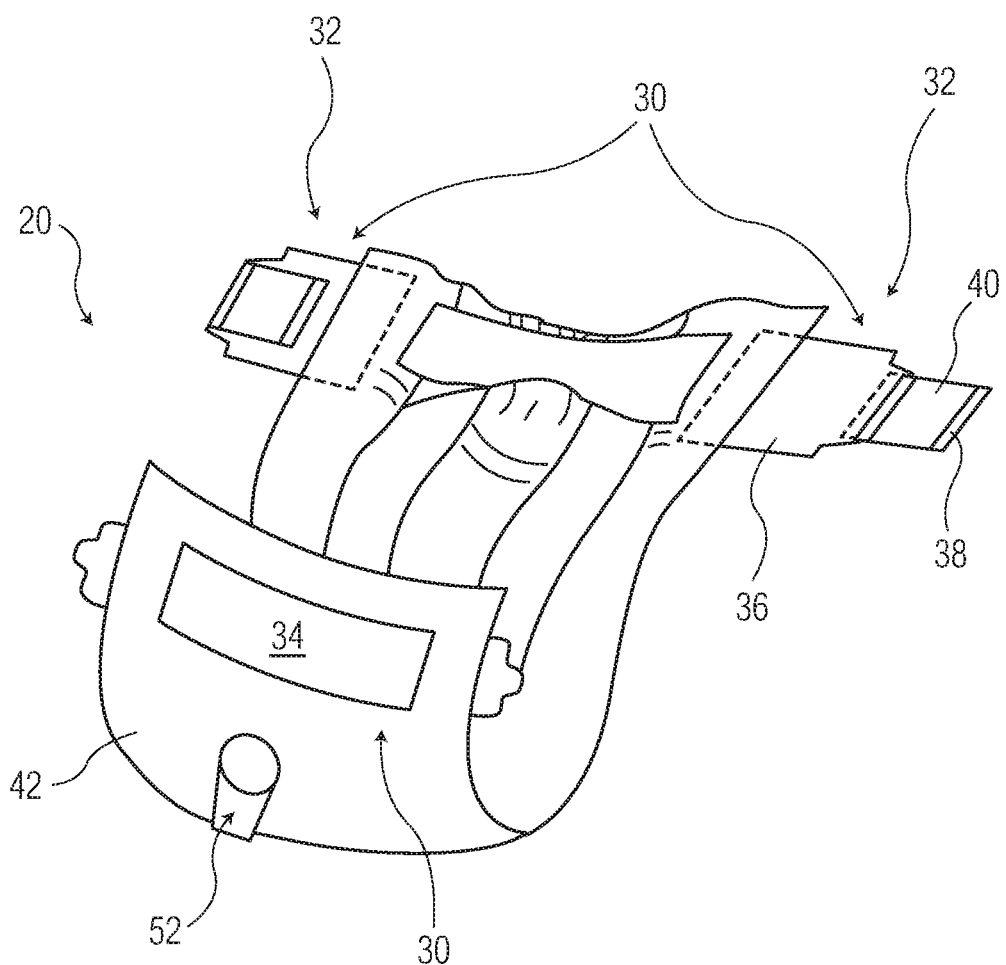
FIG. 3 is a top perspective view of an absorbent article in an unfastened, relaxed condition.

For example, FIG. 3 illustrates a fastening system 30 on an absorbent article 20 that is currently in a relaxed, unfastened condition. Although the absorbent article 20 displayed in FIG. 3 is an open diaper, the system 10 as described herein could be used with a variety of other products, including, but not limited to, other embodiments of the absorbent articles including, but not limited to, training pants, youth pants, adult incontinence garments, and feminine hygiene articles. The fastening system 30 of the absorbent article 20 can be configured to secure the absorbent article 20 about the waist of the wearer 22 while the product is being used. The fastening system 30 can include one or more back fasteners 32 and one or more front fasteners 34. As illustrated in FIG. 3, the absorbent article 20 can include two back fasteners 32 and one front fastener 34, however, other variations could be employed in a fastening system 30. The back fasteners 32 can include one or more materials bonded together to form a composite ear as is known in the art. For example, the composite fastener may be composed of a main ear component 36 (which can demonstrate elastic properties), a nonwoven carrier or base 38, and a fastening component 40 (as labeled on the right, back fastener in 32 in FIG. 3). In a packaged condition, the fastening component 40 may engage the main ear component 36, as shown in the left, back fastener 32 in FIG. 3. The fastening component 40 can be, in some embodiments, a hook material that engages with a loop material that can form the front fastener 34. Additionally or alternatively, the fastening component 40 can include a tape material that engages with the front fastener 34. It is to be understood that the front fastener 34 may be a discrete component on the outer cover 42 of the absorbent article 20, or may be a portion of the outer cover 42 itself.

When the fastening component 40 of each of the back fasteners 32 is engaged with the front fastener 34, the absorbent article 34 can be in the fastened conditioned and secured about the waist of the wearer 22. However, when the absorbent article 20 is insulted with body exudates it can be desired to replace the used absorbent article 20 with a new absorbent article 20, such as in the absorbent article change environment 18 illustrated in FIG. 1. The acoustic signature can be the sound emitted by one of the fastening components 40 of one of the back fasteners 32 being disengaged from the front fastener 34. Alternatively, the acoustic signature can be the two successive sounds emitted by both of the fastening components 40 of the two back fasteners 32 being disengaged from the front fastener 34. As noted above, this acoustic signature model can indicate that a user 24 is preparing to or is in the process 66 of an absorbent article 20 change. Of course, it is contemplated that other acoustic signatures can exist for various other types of absorbent articles that can signify a full product use of the absorbent article, such as tearing the side seam of a training pant, removing the peel strip from the adhesive of a feminine care pad, etc.

Referring back to the system 10 in FIGS. 1 and 2, the system 10 can also include an auditory capture mechanism 14. The auditory capture mechanism 14 can be a microphone. The auditory capture mechanism 14 can be configured to monitor an absorbent article change environment 18 for a potential use sound profile. The auditory capture mechanism 14 can additionally or alternatively be configured to monitor an absorbent article change environment 18 for one or more potential auditory phase cue sound profiles that can be representative of one or more phases in the absorbent article 20 change process 66, which will be described in further detail below. As noted above, in some embodiments, the system 10 can be configured to include more than one auditory capture mechanism 14 such that more than one absorbent article change environment 18 can be monitored. The auditory capture mechanism(s) 14 can be configured to capture a potential use sound profile or a potential auditory phase cue sound profile while the absorbent article 20 is being used. An auditory capture mechanism 14 can be located on the same physical device as the memory device 12 of the system 10, or the two components 12, 14 of the system 10 may be physically separated, but configured to be electronically connected. The auditory capture mechanism 14 can be configured to include or work with other known equipment such as an amplifier (not shown) for amplifying sounds within the absorbent article change environment 18 and an analog to digital converter (not shown), as known by one of ordinary skill in the art.

The system 10 can also include a processor 16. The processor 16 can be in electrical communication with the auditory capture mechanism(s) 14. The processor 16 can process via various computing types/methods, including edge-computing, fog-computing, and/or cloud computing. As such, processing by the processor 16 can take place at the edge (e.g., locally), near the edge (e.g., a gateway or nearby computing device), or in the cloud (e.g., public, private, hybrid). The processor 16 can be configured to analyze any potential use sound profile or any potential auditory phase cue captured by the auditory capture mechanism(s) 14. The analysis of a potential use sound profile or a potential auditory phase cue may vary on the particular desired acoustic signature model format. However, in general, the processor 16 can be configured to analyze a captured potential use sound profile in relation to the acoustic signature model. The processor 16 can be configured to analyze a captured potential auditory phase cue in relation to a stored auditory phase cue acoustic model.

Figure 4A:
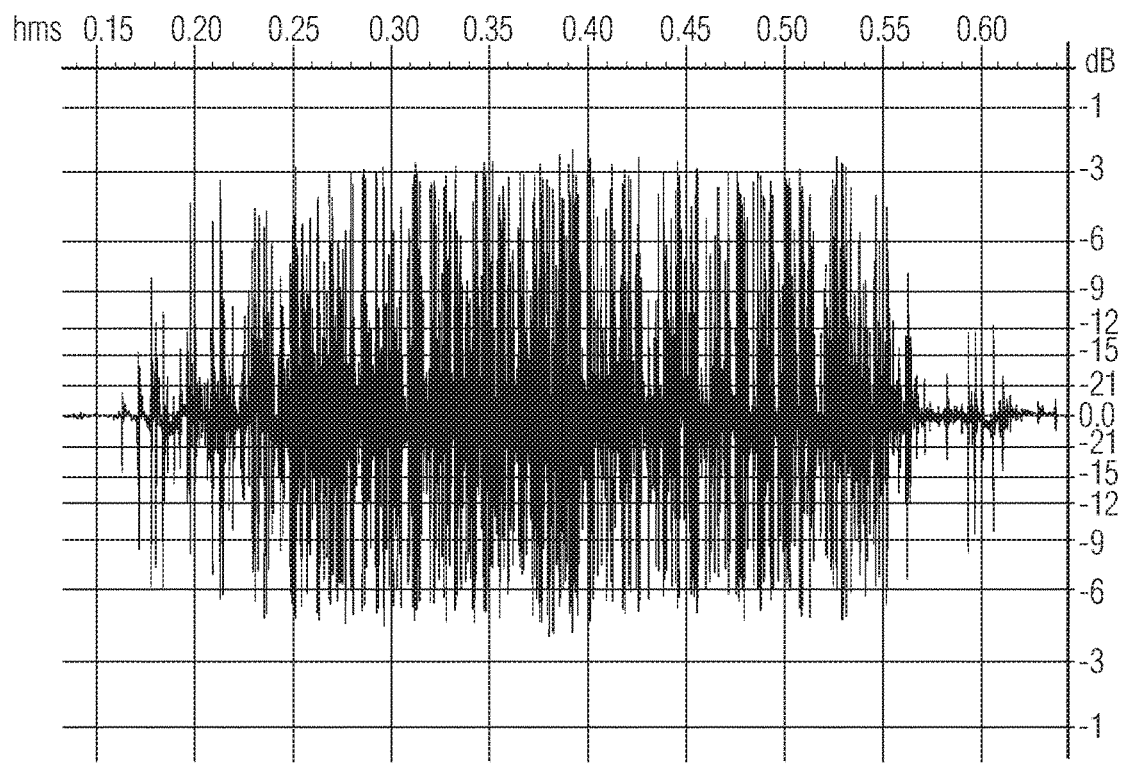
FIG. 4A is an exemplary sound profile of a fastening component of an absorbent article being unfastened providing an acoustic signature model.
Figure 4B:
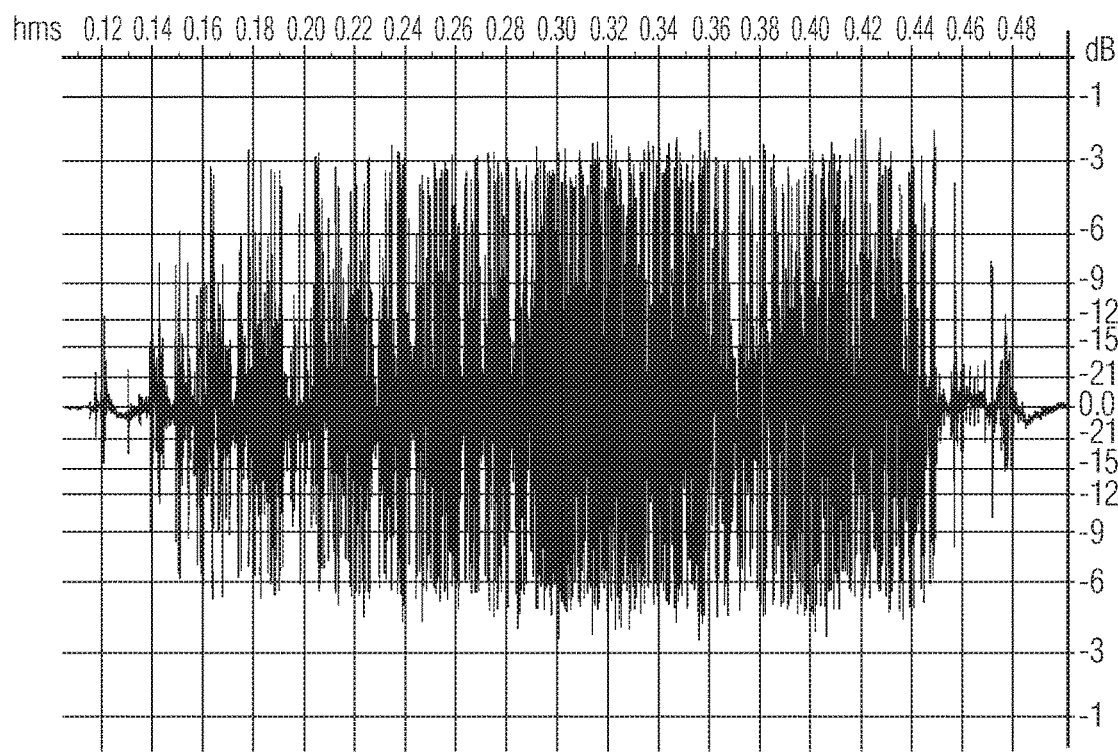
FIG. 4B is another exemplary sound profile of a fastening component of an absorbent article being unfastened providing an acoustic signature model.

As one example, the acoustic signature model can be configured as a sound profile that is documented in terms of amplitude versus time. For example, FIGS. 4A and 4B display two exemplary sound profiles captured by an auditory capture mechanism 14. FIG. 4A is representative of a sound profile of a fastening component 40 of a back fastener 32 being unfastened from a front fastener 34 on a HUGGIES® Little Snugglers Size 1 diaper and FIG. 4B is representative of a sound profile of a fastening component 40 of a back fastener 32 being unfastened from a front fastener 34 on a HUGGIES® Little Movers Size 3 diaper. In such an embodiment, the auditory capture mechanism 14 can capture a potential use sound profile as it monitors the absorbent article change environment 18. The auditory capture mechanism 14 can transmit the potential use sound profile to the processor 16 of the system 10 for analysis. Likewise, the auditory capture mechanism 14 can capture a potential auditory phase cue for a phase in the absorbent article change process as it monitors the absorbent article change environment 18 and can transmit the potential auditory phase cue to the processor 16 of the system 10 for analysis. In one example, the processor 16 can be configured to analyze a captured potential use sound profile configured as an amplitude versus time sound profile in relation to the acoustic signature model by known techniques such as spectral analysis using Fast Fourier Transform.

The processor 16 can be configured to signal a qualifying match when the captured potential use sound profile meets the acoustic signature model. The processor 16 can be configured to analyze a captured potential auditory phase cue in a similar manner. As used herein, a captured potential use sound profile can be considered to "meet" the acoustic signature model and a captured potential auditory phase cue can be considered to "meet" the respective phase auditory cue acoustic model when the analysis technique utilized by the processor 16 provides a certain confidence level that a match is obtained. For example, in the embodiment currently being described, the processor 16 can be configured to signal a qualifying match when the processor's analysis provides a 75% confidence level that the captured potential use sound profile matches the acoustic signature model that is configured as a sound profile of amplitude versus time. It is intended that the confidence level may be configured to be different than the example provided above, based on various factors including, but not limited to, the analysis technique employed by the processor 16.

Figure 5:
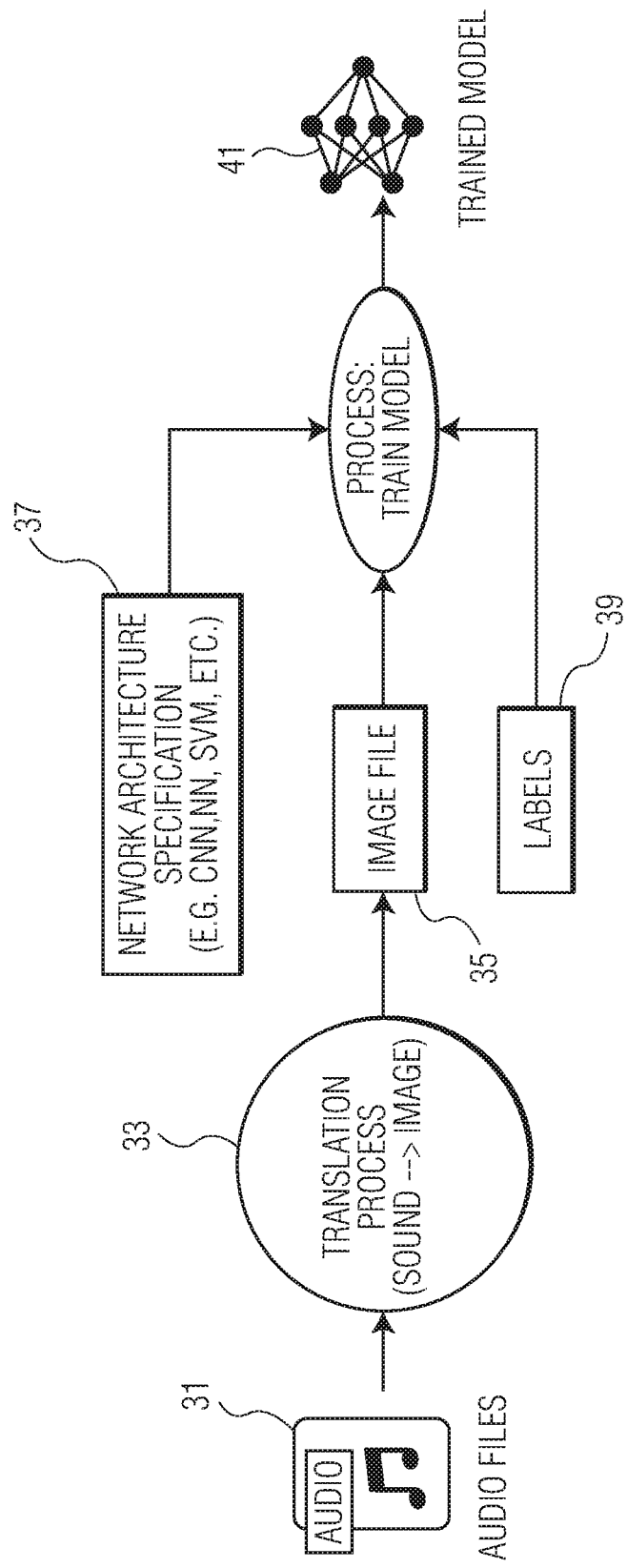
FIG. 5 is a schematic diagram of an exemplary neural network analysis that can be used to create a trained model for use as an acoustic signature model with the system as described herein.

An alternative analysis technique the processor 16 can be configured to utilize is a neural network analysis. As depicted in FIG. 5, history of audio files 31 can be put through a translation process 33, effectively translating a sound file into an image file 35. Various network architecture specifications 37, including, but not limited to, convolutional neural networks (CNN), neural networks (NN), and support vector machine (SVM), can be utilized with the image file 35 and one or more labels 39 corresponding to respective products to create a trained model 41 that can serve as an acoustic signature model for the system 10 herein. The auditory capture mechanism 14 can capture a potential use sound profile and then the processor 16 can analyze the capture potential use sound profile utilizing the trained model 41 developed from neural network analysis described above. As one example, TensorFlow is an open-source software library for machine intelligence (https://www.tensorflow.org/) that can be employed by a processor 16 to analyze the captured potential use sound profile in relation to the trained model 41 serving as the acoustic signature model. One benefit to the processor 16 employing neural network analysis techniques is that the trained model 41 can be updated based on feedback to update and/or evolve the trained model 41 providing further accuracy to the system 10.

In utilizing a trained model 41 as the acoustic signature model for the system 10, the processor 16 can be configured to signal a qualifying match when the captured potential use sound profile meets the acoustic signature model. In a CNN, for example, the analysis of the processor 16 as to whether a captured potential use sound profile meets the acoustic signature model can be based on the confidence level that a match is obtained through classification. As with most CNNs, the last layer in a CNN can be a fully-connected (FC) layer that can compute one or more class scores, with each class representing an acoustic signature model stored by the system 10. The FC layer verifies the output of a previous layer (that can represent activation maps of high level features) and determines which features most correlate to a particular class. The FC layer can take an input volume (based on the output of the proceeding layer) and can output an N-dimensional vector, where N is the number of classes that the system 10 is configured to monitor. From this, the FC layer can determine what high-level features most strongly correlate to a particular class and has particular weights so that when the processor 16 computes the products between the weights and the previous layer, a probability can be generated for the one or more classes. At the end of the CNN analysis, the processor 16 can produce an array of numbers that describe the probability (or confidence level) that an image file 35 (captured potential use sound profile) of being a certain class (or acoustic signature model) that is stored by the by the system 10.

The processor 16 can also be configured to interpret a qualifying match in view of at least one environmental input 42. An environmental input 42 can include, but is not limited to, the time of day, attitude recognition of a user 24, and attitude recognition of a wearer 22. The system 10 can be configured to categorize the time of day environmental input 42 into a daytime period and a nighttime period. Such a categorization may be helpful in determining whether to generate an output 60 to intervene in an absorbent article 20 change, and if so, what output may be most beneficial for the user 24 and/or wearer 22 to improve the experience of the absorbent article 20 change process. The daytime period can be set to correspond to the period of the time that a wearer 22 is typically awake. The nighttime period can be set to correspond to the period of the time that a wearer 22 is typically sleeping. The daytime and nighttime periods can be modified manually by a user 24, and/or the system 10 can recognize patterns in the absorbent article change environment 18 to update such daytime period and nighttime periods as a wearer 24 develops and may change its habits.

The environmental inputs 42 of attitude recognition of the user 24 and attitude recognition of a wearer 22 can be determined in a variety of ways. For example, the system 10 can be configured to employ voice recognition technology to look for certain words or phrases of a user 24 and/or wearer to help determine a current attitude of the user 24 and/or wearer 22. The system 10 can be configured to recognize crying or laughing of a wearer 22 to help determine the current attitude of the wearer 22. Additionally or alternatively, the system 10 can be configured to determine the attitude of a user 24 and/or wearer 22 based on the volume of speech or by recognizing stress in the language of a user 24 and/or wearer 22. Additionally or alternatively, the system 10 can be configured to determine the attitude of a user 24 and/or a wearer 22 based on one or more of the following types of information: analysis of a schedule/calendar, analysis of social media feeds, information from smart wearable devices (such as heart rate, activity, temperature, etc.), information from other Internet-of-Things (IoT) solutions such as sleep sensors, connected appliances, and home alarm systems, or by interfacing with third-party solutions having sentiment analysis capabilities. By determining the current attitude of a user 24 and/or wearer 22, the system 10 can help selectively generate a more appropriate output 60, as will be discussed in further detail below, to help improve the experience of an absorbent article 20 change.

The system 10 can be configured to selectively generate one or more outputs based on the qualifying match as discussed above that can be used to recognize an absorbent article 20 that is being or is about to be changed by a user 24 and at least one environmental input 42. As used herein, "selectively generate" means that the system 10 selects whether to generate an output at all, and if an output is chosen to be generated, what output should be generated. As used herein, an "output" means an action that is generated by the system 10 that can be recognized by the user 24 through a visual, an audible, and/or an olfactory sense. In some instances, the processor 16 can be configured to interpret a qualifying match in view of at least two environmental inputs 42 and the system 10 can be configured to selectively generate the first output based on the qualifying match and those two environmental inputs 42.

The system 10 can selectively generate one or more outputs 60 to help improve the experience of an absorbent article change process 66 for a user 24 and/or wearer 22 in a variety of ways. For example, the system 10 can be configured to include a speaker 62. The speaker 62 can be in electrical communication with the processor 16 and can be configured to selectively generate an output 60. Additionally or alternatively, the system 10 can include a lighting mechanism 64. The lighting mechanism can be electrically connected to the processor 16 and can be configured to selectively generate an output 60 in the form of light. It is contemplated that in some circumstances, the system 10 may be configured to generate one or more outputs 60 with a speaker 62 and/or one or more outputs 60 with the lighting mechanism 64. Additionally or alternatively, an output 60 can be generated through connection to other IoT solutions or third party solutions.

As shown in FIG. 1, in some embodiments, the lighting mechanism 64 can form part of a disposal receptacle 44, however, it is contemplated that the lighting mechanism 64 can be configured to be separate from the disposal receptacle 44. The disposal receptacle 44 can include a weight sensor 46 that is configured to weigh the contents of the disposal receptacle 44. The disposal receptacle 44 can also include a lid 48 and a lid opening sensor 50. The disposal receptacle 44 can assist a user 24 with inventory management by recording when the lid 48 is being opened through the lid opening sensor 50 and by sensing increased weight in the disposal receptacle 44 via the weight sensor 46. As will be discussed further below, the system 10 may utilize a disposal receptacle 44 and its sensors 46, 50 for helping determine which phase of the absorbent article change process 66 that a user 24 and wearer 22 are currently in.

In some embodiments, the system 10 can include a user interface 54. The user interface 54 can be configured to allow a user to interact with the system 10. The user interface 54 can allow the user 24 to manually modify certain settings and/or preferences on the system 10. For example, the user interface 54 can allow a user 24 to set specified daytime and nighttime periods, or preferences for specific outputs 60 based on the wearer(s) 22. The user interface 54 can also provide assistance to the user 24 in inventory management, such as by allowing the user 24 to document product usage that occurred outside of the absorbent article change environment(s) 18 being monitored by the auditory capture mechanism(s) 14. As illustrated in FIG. 1, the user interface 54 can be configured to be accessible from one, or more, mobile devices 56. Additionally or alternatively, the user interface 54 can be configured to be disposed on a disposal receptacle 44 or other physical aspect of the system 10.

FIG. 6 illustrates an exemplary chart of a diapering journey, or an absorbent article change process 66. FIG. 6 depicts the typical phases of the process 66 of changing an absorbent article 20, as well as typical events that may occur during each phase and the range of emotions that may occur as part of the process 66. As illustrated along the horizontal axis in FIG. 6, the process 66 can include an initiation phase 68, a preparatory phase 70, a changing phase 72, and a post-changing phase 74. Along the vertical axis, the various range of emotions that may occur during the process 66 of changing an absorbent article 20 are depicted.

In the initiation phase 68, the user 24 or the wearer 22 may provide cues that the absorbent article 20 may have an exudate in the absorbent article 20 and that the absorbent article 20 change process 66 may soon be beginning. For example, in some embodiments, the system 10 may include a body exudate detection sensor 52, such as that depicted in FIG. 3. The body exudate detection sensor 52 may provide a signal to the system 10 that a body exudate is present in the absorbent article 20, and in doing so, provide an exudate cue for the initiation phase 68. The body exudate detection sensor 52 can be a capacitance-based detector, such as disclosed in U.S. Pat. No. 8,866,624 issued to Thomas Michael Ales, III et al., or an induction-based detector, such as disclosed in U.S. Pat. No. 8,207,394 issued to Joseph Raymond Feldkamp et al., or an infra-red-based detector, such as disclosed in U.S. Pat. App. Pub. No. 2010/0168694 by Sudhanshu Gakhar et al. Of course, it is to be appreciated that other body exudate detection sensors 52 other than those mentioned directly above may be configured to be part of the system 10 discussed herein.

Another cue that the initiation phase 68 may be beginning can be provided by an initiation phase auditory cue. The system 10 can be configured such that the memory device 12 can store at least one initiation phase auditory cue acoustic model. The initiation phase auditory cue acoustic model can be representative of an acoustic profile of the initiation phase 68. The acoustic profiles that may occur during the initiation phase 68 can include word(s) or phrase(s) from the user 24 and/or the wearer 22 that an absorbent article 20 change is necessary and that the absorbent article change process 66 needs to begin. Exemplary words and/or phrases could include, "wet diaper," "dirty diaper," "diaper change," "change time," "changing time," and/or "need to change your diaper," among others. In some embodiments, the auditory capture mechanism 14 can be configured to monitor and capture the absorbent article change environment 18 for potential initiation phase auditory cue sound profiles and to capture potential initiation phase auditory cue sound profiles. The processor 16 can be configured to analyze any captured potential initiation phase auditory cue sound profiles in relation to any stored initiation phase auditory cue acoustic models and to signal a qualifying match when the captured potential initiation phase auditory cue sound profiles meets any stored initiation phase auditory cue acoustic model. The same or similar machine learning techniques as discussed above may be employed for speech recognition capability. Additionally, whether a captured potential initiation phase auditory cue sound profile meets a stored initiation phase auditory cue acoustic model is meant to be applied utilizing the same definition as noted above with respect to whether a captured potential use sound profile can be considered to meet the acoustic signature model.

In some embodiments, the system 10 can also be configured to include a proximity sensor 76 (as shown in FIG. 1) to determine if a user 24 and/or wearer 22 are approaching the absorbent article change environment 18. Such proximity sensing can provide an additional cue that the initiation phase 68 may be beginning.

Other potential auditory initiation phase cues can be in the form of feedback received from applications or skills related to absorbent articles. For example, the system 10 may receive input that a relevant IoT application or skill (that relates to, such as, providing information related to changing an absorbent article 20, care of a wearer 22, or parenting) has been opened or queried.

The preparatory phase 70 of the absorbent article changing process 66 occurs after the initiation phase 68. The system 10 may be configured to recognize the preparatory phase 70 through a variety of different preparatory phase auditory cues. For example, the system 10 can be configured such that the memory device 12 is configured to store at least one preparatory phase auditory cue acoustic model that is representative of an acoustic profile of the preparatory phase 70. Acoustic profiles of the preparatory phase 70 can include, but are not limited to, acoustic profiles of the following activities: unfastening a fastener 32 of the absorbent article 20 from the fastened condition, removing a new absorbent article 20 from packaging, placing the wearer on a changing area (such as a changing pad 78), and removal of clothing from the wearer 22.

The auditory capture mechanism 14 can be configured to monitor the absorbent article change environment 18 for potential preparatory phase auditory cue sound profiles and to capture potential preparatory phase auditory cue sound profiles. The processor 16 can be configured to analyze a captured potential preparatory phase auditory cue sound profile in relation to the stored preparatory phase auditory cue acoustic model(s) and to signal a qualifying match when a captured potential preparatory phase auditory cue sound profile meets a stored preparatory phase auditory cue acoustic model.

The system 10 can be configured to selectively generate one or more outputs 60 during the preparatory phase 70 to improve the experience during the preparatory phase 70 of the absorbent article change process 66. The output(s) 60 generated by the system 10 can be selectively generated after the processor 16 signals a qualifying match of a captured potential use sound profile meeting the absorbent article acoustic signature model or a qualifying match when the captured potential preparatory phase cue sound profile meets the at least one stored preparatory phase auditory cue acoustic model. Such a qualifying match can indicate that the preparatory phase 70 is likely started and the user 24 and/or wearer 22 may benefit from intervention in the absorbent article change process 66. The output 60 that may be selectively generated can be configured based on such a qualifying match and at least one environmental input 42, as described above.

For example, in one scenario, the system 10 may receive an environmental input 42 that it is currently the daytime period. After receiving a qualifying match as described above and considering the environmental input 42 of a daytime period, the system 10 can be configured to have the speaker 62 selectively generate an output 60, such as, but not limited to: music, nursery rhymes, auditory stories, animal sounds, and alpha-numeric instructional lessons. These or other outputs 60 can be generated through connection to other IoT solutions or third party solutions, including, but not limited to, applications or skills for smart speaker devices. Additionally, an output 60 could be the launch of an application or skill itself.

In another scenario, the system 10 may receive an environmental input 42 that it is currently the nighttime period. After receiving a qualifying match as described above and considering the environmental input 42 of a nighttime period, the system 10 can be configured to have the speaker 62 selectively generate an output 60, such as, but not limited to: music and white noise. In some embodiments, the system 10 may be configured such that when it receives an environmental input 42 that it is currently the nighttime period, the system 10 will only be configured to have the speaker 62 selectively generate an output 60, such as music or white noise, when the system 10 also receives an environmental input 42 of the attitude recognition of the user 24 or the wearer 22 as crying, stressed, or disturbed. In other words, the system 10 can be configured to selectively generate no output 60 at all when it is the nighttime period and the user 24 and/or wearer 22 remain quiet to facilitate a quiet nighttime change, or be configured to help provide calming music and/or white noise based on the system 10 receiving an environmental input 42 to help calm the wearer 22 and/or the user 24 if the system 10 receives an environmental input 42 signifying that the wearer 22 or the user 24 is crying, stressed, or disturbed.

Additionally, after receiving a qualifying match as described above, if the system 10 receives an environmental input 42 signifying that it is currently the nighttime period, the system 10 can generate an output 60 from the lighting mechanism 64 in the form of light. This visual output 60 can provide assistance to the user 24 to facilitate the change of the absorbent article 20, and can be selectively generated with or without the audible output(s) 60 described above.

Another exemplary output 60 that can be generated by the system 10 can include an output 60 that is recognizable by a user 24 and/or wearer 22 through their olfactory senses. The system 10 can be configured to include an olfactory output mechanism 80. The olfactory output mechanism 80 can be configured in the form of equipment that is separate from other components of the system 10 and be in electrical communication with the processor 16 (such as depicted in FIG. 1), or it can be integrated with one or more other components forming the system 10. The system 10 can be configured to selectively generate an output 60 from the olfactory output mechanism 80 that the wearer 22 and/or user 24 can smell. Such an output 60 can help provide a calming scent and/or cover scent to cover the smell of body exudates, improving the experience of the absorbent article change process 66 for the user 24 and/or wearer 22. The system 10 can be configured to selectively generate an output 60 from the olfactory output mechanism 80 after receiving a qualifying match as described above and in response to certain confirmed cues. For example, the system 10 can have voice recognition capability and can have the memory device 12 configured to store certain word(s) or phrase(s), such as "stinky diaper" or "smelly", that may represent a situation to have such an olfactory output 60 selectively generated. The auditory capture mechanism 14 can be configured to monitor the absorbent article change environment 18 for the potential use of such word(s) or phrase(s) and capture such potential use of such word(s) or phrase(s), and the processor 16 can be configured to analyze the captured word(s) or phrase(s) in relation to the stored word(s) or phrase(s). If such word(s) or phrase(s) are confirmed through a captured potential word(s) or phrase(s) meeting a stored word(s) or phrase(s) through the voice recognition capability, then the system 10 may be configured to selectively generate such an olfactory output 60 through the olfactory output mechanism 80.

Referring back to FIG. 6, the preparatory phase 70 is followed by the changing phase 72 in the absorbent article change process 66. The changing phase 72 can be recognized by the system 10 through one or more changing phase auditory cues. The memory device 12 can be configured to store at least one changing phase auditory cue acoustic model that is representative of an acoustic profile of the changing phase 72. Acoustic profiles of the changing phase 72 can include, but are not limited to, acoustic profiles of the following activities: opening packaging (e.g., box, bag, etc.) of new absorbent articles, removing a new absorbent article 20 from packaging, unfolding a new absorbent article 20, user language associated with contents of the absorbent article 20 being changed, a lid 82 of a wet wipe package 84 being opened, a wet wipe 86 being removed from a wet wipe package 84, rolling of the absorbent article 20 for disposal, opening an ointment lid, and application of ointment to the wearer.

The auditory capture mechanism 14 can be configured to monitor the absorbent article change environment(s) 18 for potential changing phase auditory cue sound profiles and to capture potential changing phase auditory cue sound profiles. The processor 16 can be configured to analyze a captured potential changing phase auditory cue sound profile in relation to the stored changing phase auditory cue acoustic model(s) and to signal a qualifying match when a captured potential changing phase auditory cue sound profile meets a stored changing phase auditory cue acoustic model.

The system 10 can be configured to selectively generate one or more outputs 60 during the changing phase 72 to improve the experience during the changing phase 72 of the absorbent article change process 66. If one or more outputs 60 were selectively generated during the preparatory phase 70, the system 10 can continue to generate such output(s) 60. Alternatively, the system 10 can be configured to selectively generate one or more outputs 60 of first instance after the processor 16 signals a qualifying match of a captured potential changing phase auditory cue sound profile in relation to the stored changing phase auditory cue acoustic model(s). The output(s) 60 generated by the system 10 during the changing phase 72 based on such a qualifying match and at least one environmental input 42, as described above.

The post-changing phase 74 is the last phase of the absorbent article change process 66 before the user 24 and wearer 22 can "return to the moment," or in other words, return to the activities that each were engaged in prior to the process 66 beginning. The post-changing phase 74 can be recognized through one or more post-changing phase cues, which may be auditory or non-auditory in nature. The memory device 12 can be configured to store at least one post-changing phase auditory cue acoustic model that is representative of an acoustic profile of the post-changing phase. Acoustic profiles of the post-changing phase can include, but are not limited to, acoustic profiles of the following activities: fastening a new absorbent article 20, disposal of the used absorbent article 20, donning clothing, closing a lid 82 of a wet wipes package 84, cleaning the absorbent article change environment 18, and leaving the absorbent article change environment 18. The fastening of the new absorbent article 20 can include sound profiles associated with removing the fastening component 40 from the main ear component 36, applying the fastening components 40 of the back fasteners 30 to the front fastener 34, and adjusting such fasteners for fit. The disposal of the absorbent article 20 can provide an acoustic profile that is unique to the absorbent article being received in a trash bin or disposal receptacle 44, or can be an acoustic profile of the lid 48 of the disposal receptacle 44 being opened and/or closed.

The auditory capture mechanism 14 can be configured to monitor the absorbent article change environment(s) 18 for potential post-changing phase auditory cue sound profiles and to capture potential post-changing phase auditory cue sound profiles. The processor 16 can be configured to analyze a captured potential post-changing phase auditory cue sound profile in relation to the stored post-changing phase auditory cue acoustic model(s) and to signal a qualifying match when the captured potential post-changing phase auditory cue sound profile meets a stored post-changing phase auditory cue acoustic model.

Other non-acoustic cues that can signify the post-changing phase 74 can include the sensing of the disposal of the used absorbent article 20 through the sensing mechanisms on the disposal receptacle 44, such as the lid opening sensor 50 or the weight sensor 46 described above. These cues can also provide an indication that the post-changing phase 74 is at or near completion.

The system 10 can be configured to stop generating one or more outputs 60 that were selectively generated by the system 10 in previous phases 68, 70, 72 of the absorbent article change process 66 after the post-changing phase 74 is completed. In one embodiment, the system 10 can be configured such that the processor 16 can send a signal to stop generating an output 60 upon a qualifying match confirming the post-changing phase 74 as described above. Such a signal could also be sent upon the system 10 confirming a non-auditory cue as described above. In some embodiments, the system 10 can be configured such that the output 60 can continue to be generated for a specified period of time after the system 10 confirms the post-changing phase 74. For example, the system 10 could be configured to continue to generate one or more outputs for a period of 30 seconds, or 1 minute, or 2 minutes after the confirmation of the post-changing phase 74 identified above. A delay in stopping the output(s) 60 previously generated can ease the transition out of the post-changing phase 74 as the user 24 and wearer 22 complete the absorbent article change process 66.

The system 10 can provide multiple benefits of intervening in the absorbent article change process 66 to improve the experience of the user 24 and wearer 22. The system 10 can improve the interaction/connection between the user 24 and the wearer 22 during the absorbent article change process 66. This improved interaction/connection can improve the emotional experience of the user 24 and/or the wearer 22, potentially removing stress from the user 24 and/or the wearer 22. The system 10 can also increase the ease of which a change occurs through various outputs 60, for example, such as by providing light when necessary, and/or providing calming and/or cover scents to improve the olfactory experience of an absorbent article change process 66. Importantly, the system 10 can be configured to selectively intervene in such a process to provide outputs 60 that will enhance the experience when necessary, but refrain from generating output(s) 60 when not necessary and/or desired by the user 24 and/or wearer 22.

The system 10 can also provide the benefit of being customizable when there is more than one user 24 and/or wearer 22 that may be utilizing the system 10. The system 10 can be configured to differentiate between different wearers 22 and different users 24 to provide customizable or preferred outputs 60 for a more enjoyable and effective intervention into the absorbent article change process 66. For example, the system 10 can include voice recognition capability that can differentiate between wearers 22 and/or users 24 based on auditory recognition of voices of different wearers 22 and/or users 24, respectively. The system 10 can also be configured to identify and confirm auditory cues that differ between the sizes of the absorbent article 20 and/or the specific absorbent article 20 being used by such wearer 22 (e.g., different acoustic profiles for back fasteners 32 being disengaged from front fastener 34 based on size of absorbent article 20 and/or type of absorbent article 20), and by such, recognize which wearer 22 is about to engage in or is engaging in the absorbent article change process 66. After such recognition, the system 10 can be configured to provide a different output 60 for a wearer 22 that may be customized for that wearer 22. As an example, the system 10 may selectively generate a different output 60 for a wearer 22 that is three months old, such as a nursery rhyme output 60, as compared to an output 60 for a wearer 22 that is three years old, which may be alpha-numeric instruction type output 60. In doing so, the system 10 can provide outputs 60 that are tailored to the specific wearer 22 and/or user 24 to provide a more enjoyable and effective experience.

EMBODIMENTS

Embodiment 1: A system comprising: a memory device configured to store an absorbent article acoustic signature model, the absorbent article acoustic signature model being indicative of a potential change of the absorbent article and being emitted from the absorbent article during use of the absorbent article; an auditory capture mechanism configured to monitor an absorbent article change environment for a potential use sound profile and to capture the potential use sound profile while the product is being used; and a processor in electrical communication with the auditory capture mechanism, the processor being configured to analyze the captured potential use sound profile in relation to the absorbent article acoustic signature model, the processor further configured to signal a first qualifying match when the captured potential use sound profile meets the absorbent article acoustic signature model, the processor being further configured to interpret the first qualifying match in view of at least one environmental input, the at least one environmental input being selected from the group consisting of: time of day, attitude recognition of a wearer of the absorbent article, and attitude recognition of a user of the absorbent article; wherein the system is configured to selectively generate a first output based on the first qualifying match and the at least one environmental input, the first output being recognizable by the user through visual, audible, or olfactory senses.

Embodiment 2: The system of embodiment 1, wherein the absorbent article acoustic signature model is representative of a fastener of the absorbent article being unfastened from a fastened condition of the absorbent article.

Embodiment 3: The system of embodiment 1 or 2, wherein the processor is configured to interpret the first qualifying match in view of at least two environmental inputs, and wherein the system is configured to selectively generate the first output based on the first qualifying match and the at least two environmental inputs.

Embodiment 4: The system of any one of the preceding embodiments, wherein the system further comprises a speaker, the speaker being in electrical communication with the processor and being configured to selectively generate the first output.

Embodiment 5: The system of embodiment 4, wherein the at least one environmental input is the time of day, the system being configured to categorize the time of day into a daytime period and a nighttime period, the system being configured to have the speaker selectively generate the first output during the daytime period, and wherein the first output is selected from the group consisting of: music, nursery rhymes, auditory stories, animal sounds, and alpha-numeric instructional lessons.

Embodiment 6: The system of embodiment 4, wherein the at least one environmental input is the time of day, the system being configured to categorize the time of day into a daytime period and a nighttime period, the system being configured to have the speaker selectively generate the first output during the nighttime period, and wherein the first output is selected from the group consisting of: music and white noise.

Embodiment 7: The system of any one of the preceding embodiments, wherein the system further comprises a lighting mechanism, the lighting mechanism being electrically connected to the processor and being configured to selectively generate a second output based on the time of day, the second output being light.

Embodiment 8: The system of any one of the preceding embodiments, wherein the system is further configured to recognize an exudate cue of an initiation phase, the exudate cue comprising at least one of exudate related user language and an electronic signal associated with a body exudate detection sensor on the absorbent article.

Embodiment 9: The system of any one of the preceding embodiments, wherein the memory device is further configured to store at least one preparatory phase auditory cue acoustic model, the at least one preparatory phase auditory cue acoustic model being representative of an acoustic profile of the preparatory phase, the acoustic profile of the preparatory phase being selected from the group of acoustic profiles consisting of: unfastening a fastener of the absorbent article from the fastened condition, removing a new absorbent article from packaging, placing the wearer on a changing area, and removal of clothing from the wearer; wherein the auditory capture mechanism is further configured to monitor the absorbent article change environment for potential preparatory phase auditory cue sound profiles and to capture potential preparatory phase auditory cue sound profiles; and wherein the processor is further configured to analyze a captured potential preparatory phase auditory cue sound profile in relation to the at least one stored preparatory phase auditory cue acoustic model and to signal a second qualifying match when the captured potential preparatory phase auditory cue sound profile meets the at least one stored preparatory phase auditory cue acoustic model.

Embodiment 10: The system of any one of the preceding embodiments, wherein the memory device is further configured to store at least one changing phase auditory cue acoustic model, the at least one changing phase auditory cue acoustic model being representative of an acoustic profile of the changing phase, the acoustic profile of the changing phase being selected from the group of acoustic profiles consisting of: opening packaging of new absorbent articles, removing a new absorbent article from packaging, unfolding a new absorbent article, user language associated with contents of the absorbent article being changed, opening of a lid of a wet wipe package, removing a wet wipe from a wet wipe package, rolling of the absorbent article 20 for disposal, opening an ointment lid, and application of ointment to the wearer; wherein the auditory capture mechanism is further configured to monitor the absorbent article change environment for potential changing phase auditory cue sound profiles and to capture potential changing phase auditory cue sound profiles, and wherein the processor is further configured to analyze a captured potential changing phase auditory cue sound profile in relation to the at least one stored changing phase auditory cue acoustic model and to signal a third qualifying match when the captured potential changing phase auditory cue sound profile meets the at least one stored changing phase auditory cue acoustic model.

Embodiment 11: The system of any one of the preceding embodiments, wherein the memory device is further configured to store at least one post-changing phase auditory cue acoustic model, the at least one post-changing phase auditory cue acoustic model being representative of an acoustic profile of the post-changing phase, the acoustic profile of the post-changing phase being selected from the group of acoustic profiles consisting of: fastening a new absorbent article, disposing of the absorbent article, donning clothing, closing a lid of a wet wipes package, cleaning the absorbent article change environment, and leaving the absorbent article change environment; wherein the auditory capture mechanism is further configured to monitor the absorbent article change environment for potential post-changing phase auditory cue sound profiles and to capture potential post-changing phase auditory cue sound profiles, wherein the processor is further configured to analyze a captured potential post-changing phase auditory cue sound profile in relation to the at least one stored post-changing phase auditory cue acoustic model and to signal a fourth qualifying match when the captured potential post-changing phase auditory cue sound profile meets the at least one stored post-changing phase auditory cue acoustic model, and wherein, if the first output was being generated by the system, the processor is configured to send a signal to stop generating the first output upon the signaling of the fourth qualifying match.

Embodiment 12: A system for intervening in an absorbent article change process by a user, the absorbent article change process including an initiation phase, a preparatory phase, a changing phase, and a post-changing phase, the system comprising: a memory device configured to store at least one preparatory phase auditory cue acoustic model, the at least one preparatory phase auditory cue acoustic model being representative of an acoustic profile of the preparatory phase; an auditory capture mechanism configured to monitor an absorbent article change environment for potential preparatory phase auditory cue sound profiles and to capture potential preparatory phase auditory cue sound profiles; and a processor in electrical communication with the auditory capture mechanism, the processor being configured to analyze a captured potential preparatory phase cue sound profile in relation to the at least one stored preparatory phase auditory cue acoustic model, the processor further configured to signal a first qualifying match when the captured potential preparatory phase cue sound profile meets the at least one stored preparatory phase auditory cue acoustic model, the processor being further configured to interpret the first qualifying match in view of at least one environmental input; wherein the system is configured to selectively generate a first output based on the first qualifying match and the at least one environmental input, the first output being recognizable by the user through visual, audible, or olfactory senses.

Embodiment 13: The system of embodiment 12, wherein the acoustic profile of the preparatory phase is selected from the group of acoustic profiles consisting of: unfastening a fastener of the absorbent article from the fastened condition, removing a new absorbent article from packaging, placing the wearer on a changing area, and removal of clothing from the wearer.

Embodiment 14: The system of embodiment 12 or 13, wherein the environmental input is selected from the group consisting of: time of day, attitude recognition of a wearer of the absorbent article, and attitude recognition of a user of the absorbent article.

Embodiment 15: The system of any one of embodiments 12-14, wherein the processor is configured to interpret the first qualifying match in view of at least two environmental inputs, and wherein the system is configured to selectively generate the first output based on the first qualifying match and the at least two environmental inputs.

Embodiment 16: The system of any one of embodiments 12-15, wherein the system further comprises a speaker, the speaker being in electrical communication with the processor and being configured to selectively generate the first output.

Embodiment 17: The system of any one of embodiments 12-16, wherein the system is further configured to recognize an exudate cue of the initiation phase, the exudate cue comprising at least one of exudate related user language and an electronic signal associated with a body exudate detection sensor on the absorbent article.

Embodiment 18: The system of any one of embodiments 12-17, wherein the memory device is further configured to store at least one changing phase auditory cue acoustic model, the at least one changing phase auditory cue acoustic model being representative of an acoustic profile of the changing phase, the acoustic profile of the changing phase being selected from the group of acoustic profiles consisting of: opening packaging of new absorbent articles, removing a new absorbent article from packaging, unfolding a new absorbent article, user language associated with contents of the absorbent article being changed, opening of a lid of a wet wipe package, removing a wet wipe from a wet wipe package, rolling of the absorbent article 20 for disposal, opening an ointment lid, and application of ointment to the wearer; and wherein the auditory capture mechanism is further configured to monitor the absorbent article change environment for potential changing phase auditory cue sound profiles and to capture potential changing phase auditory cue sound profiles; and wherein the processor is further configured to analyze a captured potential changing phase auditory cue sound profile in relation to the at least one stored changing phase auditory cue acoustic model and to signal a third qualifying match when the captured potential changing phase auditory cue sound profile meets the at least one stored changing phase auditory cue acoustic model.

Embodiment 19: The system of any one of embodiments 12-18, wherein the memory device is further configured to store at least one post-changing phase auditory cue acoustic model, the at least one post-changing phase auditory cue acoustic model being representative of an acoustic profile of the post-changing phase, the acoustic profile of the post-changing phase being selected from the group of acoustic profiles consisting of: fastening a new absorbent article, disposing of the absorbent article, donning clothing, closing a lid of a wet wipes package, cleaning the absorbent article change environment, and leaving the absorbent article change environment; wherein the auditory capture mechanism is further configured to monitor the absorbent article change environment for potential post-changing phase auditory cue sound profiles and to capture potential post-changing phase auditory cue sound profiles; wherein the processor is further configured to analyze a captured potential post-changing phase auditory cue sound profile in relation to the at least one stored post-changing phase auditory cue acoustic model and to signal a third qualifying match when the captured potential post-changing phase auditory cue sound profile meets the at least one stored post-changing phase auditory cue acoustic model, and wherein, if the first output was being generated by the system, the processor is configured to send a signal to stop generating the first output upon the signaling of the fourth qualifying match.

Embodiment 20: A computer program product comprising code embodied on a non-transitory computer-readable medium and configured to be executed on one or more processors, the computer program product being configured to perform operations of: storing an absorbent article acoustic model, the absorbent article acoustic signature model being indicative of a potential change of the absorbent article and being emitted from the absorbent article during use of the absorbent article; monitoring an absorbent article change environment for a potential use sound profile; capturing the potential use sound profile with an auditory capture mechanism; analyzing the captured potential use sound profile in relation to the stored absorbent article acoustic signature model; signaling a first qualifying match when the captured potential use sound profile meets the stored absorbent article acoustic signature model; interpreting the first qualifying match in view of at least one environmental input, the at least one environmental input being selected from the group consisting of: time of day, attitude recognition of a wearer of the absorbent article, and attitude recognition of a user of the absorbent article; and selectively generating a first output based on the first qualifying match and the at least one environmental input, the first output being recognizable by the user through visual, audible, or olfactory senses.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A system comprising:
a memory device configured to store an absorbent article acoustic signature model, the absorbent article acoustic signature model being indicative of a potential change of the absorbent article and being emitted from the absorbent article during use of the absorbent article;
an auditory capture mechanism configured to monitor an absorbent article change environment for a potential use sound profile and to capture the potential use sound profile while an absorbent article is being used; and
a processor in electrical communication with the auditory capture mechanism, the processor being configured to analyze the captured potential use sound profile in relation to the absorbent article acoustic signature model, the processor further configured to signal a first qualifying match when the captured potential use sound profile meets the absorbent article acoustic signature model, the processor being further configured to interpret the first qualifying match in view of at least one environmental input, the at least one environmental input being selected from the group consisting of: time of day, attitude recognition of a wearer of the absorbent article, and attitude recognition of a user of the absorbent article;
wherein the system is configured to selectively generate a first output based on the first qualifying match and the at least one environmental input, the first output being recognizable by the user through visual, audible, or olfactory senses.

2. The system of claim 1, wherein the absorbent article acoustic signature model is representative of a fastener of the absorbent article being unfastened from a fastened condition of the absorbent article.

3. The system of claim 1, wherein the processor is configured to interpret the first qualifying match in view of at least two environmental inputs, the at least two environmental inputs being selected from the group consisting of: time of day, attitude recognition of a wearer of the absorbent article, and attitude recognition of a user of the absorbent article, and wherein the system is configured to selectively generate the first output based on the first qualifying match and the at least two environmental inputs.

4. The system of claim 1, wherein the system further comprises a speaker, the speaker being in electrical communication with the processor and being configured to selectively generate the first output.

5. The system of claim 4, wherein the at least one environmental input is the time of day, the system being configured to categorize the time of day into a daytime period and a nighttime period, the system being configured to have the speaker selectively generate the first output during the daytime period, and wherein the first output is selected from the group consisting of: music, nursery rhymes, auditory stories, animal sounds, and alpha-numeric instructional lessons.

6. The system of claim 4, wherein the at least one environmental input is the time of day, the system being configured to categorize the time of day into a daytime period and a nighttime period, the system being configured to have the speaker selectively generate the first output during the nighttime period, and wherein the first output is selected from the group consisting of: music and white noise.

7. The system of claim 6, wherein the system further comprises a light mechanism, the light mechanism being electrically connected to the processor and being configured to selectively generate a second output based on the time of day, the second output being light.

8. The system of claim 1, wherein the system is further configured to recognize an exudate cue of an initiation phase, the exudate cue comprising at least one of exudate related user language and an electronic signal associated with a body exudate detection sensor on the absorbent article.

9. The system of claim 1, wherein the memory device is further configured to store at least one preparatory phase auditory cue acoustic model, the at least one preparatory phase auditory cue acoustic model being representative of an acoustic profile of the preparatory phase, the acoustic profile of the preparatory phase being selected from the group of acoustic profiles consisting of: unfastening a fastener of the absorbent article from the fastened condition, removing a new absorbent article from packaging, placing the wearer on a changing area, and removal of clothing from the wearer;
wherein the auditory capture mechanism is further configured to monitor the absorbent article change environment for potential preparatory phase auditory cue sound profiles and to capture potential preparatory phase auditory cue sound profiles; and
wherein the processor is further configured to analyze a captured potential preparatory phase auditory cue sound profile in relation to the at least one stored preparatory phase auditory cue acoustic model and to signal a second qualifying match when the captured potential preparatory phase auditory cue sound profile meets the at least one stored preparatory phase auditory cue acoustic model.

10. The system of claim 1, wherein the memory device is further configured to store at least one changing phase auditory cue acoustic model, the at least one changing phase auditory cue acoustic model being representative of an acoustic profile of the changing phase, the acoustic profile of the changing phase being selected from the group of acoustic profiles consisting of: opening packaging of new absorbent articles, removing a new absorbent article from packaging, unfolding a new absorbent article, user language associated with contents of the absorbent article being changed, opening of a lid of a wet wipe package, removing a wet wipe from a wet wipe package, rolling of the absorbent article for disposal, opening an ointment lid, and application of ointment to the wearer;
wherein the auditory capture mechanism is further configured to monitor the absorbent article change environment for potential changing phase auditory cue sound profiles and to capture potential changing phase auditory cue sound profiles, and
wherein the processor is further configured to analyze a captured potential changing phase auditory cue sound profile in relation to the at least one stored changing phase auditory cue acoustic model and to signal a third qualifying match when the captured potential changing phase auditory cue sound profile meets the at least one stored changing phase auditory cue acoustic model.

11. The system of claim 1, wherein the memory device is further configured to store at least one post-changing phase auditory cue acoustic model, the at least one post-changing phase auditory cue acoustic model being representative of an acoustic profile of the post-changing phase, the acoustic profile of the post-changing phase being selected from the group of acoustic profiles consisting of: fastening a new absorbent article, disposing of the absorbent article, donning clothing, closing a lid of a wet wipes package, cleaning the absorbent article change environment, and leaving the absorbent article change environment;
wherein the auditory capture mechanism is further configured to monitor the absorbent article change environment for potential post-changing phase auditory cue sound profiles and to capture potential post-changing phase auditory cue sound profiles,
wherein the processor is further configured to analyze a captured potential post-changing phase auditory cue sound profile in relation to the at least one stored post-changing phase auditory cue acoustic model and to signal a fourth qualifying match when the captured potential post-changing phase auditory cue sound profile meets the at least one stored post-changing phase auditory cue acoustic model, and wherein, if the first output was being generated by the system, the processor is configured to send a signal to stop generating the first output upon the signaling of the fourth qualifying match.

12. A system for intervening in an absorbent article change process by a user, the absorbent article change process including an initiation phase, a preparatory phase, a changing phase, and a post-changing phase, the system comprising:
a memory device configured to store at least one preparatory phase auditory cue acoustic model, the at least one preparatory phase auditory cue acoustic model being representative of an acoustic profile of the preparatory phase;

an auditory capture mechanism configured to monitor an absorbent article change environment for potential preparatory phase auditory cue sound profiles and to capture potential preparatory phase auditory cue sound profiles; and a processor in electrical communication with the auditory capture mechanism, the processor being configured to analyze a captured potential preparatory phase cue sound profile in relation to the at least one stored preparatory phase auditory cue acoustic model, the processor further configured to signal a first qualifying match when the captured potential preparatory phase cue sound profile meets the at least one stored preparatory phase auditory cue acoustic model, the processor being further configured to interpret the first qualifying match in view of at least one environmental input;

wherein the system is configured to selectively generate a first output based on the first qualifying match and the at least one environmental input, the first output being recognizable by the user through visual, audible, or olfactory senses.

13. The system of claim 12, wherein the acoustic profile of the preparatory phase is selected from the group of acoustic profiles consisting of: unfastening a fastener of the absorbent article from the fastened condition, removing a new absorbent article from packaging, placing a wearer on a changing area, and removal of clothing from the wearer.

14. The system of claim 13, wherein the system further comprises a speaker, the speaker being in electrical communication with the processor and being configured to selectively generate the first output.

15. The system of claim 13, wherein the system is further configured to recognize an exudate cue of the initiation phase, the exudate cue comprising at least one of exudate related user language and an electronic signal associated with a body exudate detection sensor on the absorbent article.

16. The system of claim 13, wherein the memory device is further configured to store at least one changing phase auditory cue acoustic model, the at least one changing phase auditory cue acoustic model being representative of an acoustic profile of the changing phase, the acoustic profile of the changing phase being selected from the group of acoustic profiles consisting of: opening packaging of new absorbent articles, removing a new absorbent article from packaging, unfolding a new absorbent article, user language associated with contents of the absorbent article being changed, opening of a lid of a wet wipe package, removing a wet wipe from a wet wipe package, rolling of the absorbent article for disposal, opening an ointment lid, and application of ointment to the wearer; and wherein the auditory capture mechanism is further configured to monitor the absorbent article change environment for potential changing phase auditory cue sound profiles and to capture potential changing phase auditory cue sound profiles; and wherein the processor is further configured to analyze a captured potential changing phase auditory cue sound profile in relation to the at least one stored changing phase auditory cue acoustic model and to signal a second qualifying match when the captured potential changing phase auditory cue sound profile meets the at least one stored changing phase auditory cue acoustic model.

17. The system of claim 13, wherein the memory device is further configured to store at least one post-changing phase auditory cue acoustic model, the at least one post-changing phase auditory cue acoustic model being representative of an acoustic profile of the post-changing phase, the acoustic profile of the post-changing phase being selected from the group of acoustic profiles consisting of: fastening a new absorbent article, disposing of the absorbent article, donning clothing, closing a lid of a wet wipes package, cleaning the absorbent article change environment, and leaving the absorbent article change environment;

wherein the auditory capture mechanism is further configured to monitor the absorbent article change environment for potential post-changing phase auditory cue sound profiles and to capture potential post-changing phase auditory cue sound profiles, wherein the processor is further configured to analyze a captured potential post-changing phase auditory cue sound profile in relation to the at least one stored post-changing phase auditory cue acoustic model and to signal a third qualifying match when the captured potential post-changing phase auditory cue sound profile meets the at least one stored post-changing phase auditory cue acoustic model, and wherein, if the first output was being generated by the system, the processor is configured to send a signal to stop generating the first output upon the signaling of the third qualifying match.

18. The system of claim 12, wherein the at least one environmental input is selected from the group consisting of: time of day, attitude recognition of a wearer of the absorbent article, and attitude recognition of a user of the absorbent article.

19. The system of claim 18, wherein the processor is configured to interpret the first qualifying match in view of at least two environmental inputs, the at least two environmental inputs being selected from the group consisting of: time of day, attitude recognition of a wearer of the absorbent article, and attitude recognition of a user of the absorbent article, and wherein the system is configured to selectively generate the first output based on the first qualifying match and the at least two environmental inputs.

20. A computer program product comprising code embodied on a non-transitory computer-readable medium and configured to be executed on one or more processors, the computer program product being configured to perform operations of:

storing an absorbent article acoustic model, the absorbent article acoustic signature model being indicative of a potential change of the absorbent article and being emitted from the absorbent article during use of the absorbent article;

monitoring an absorbent article change environment for a potential use sound profile;

capturing the potential use sound profile with an auditory capture mechanism;

analyzing the captured potential use sound profile in relation to the stored absorbent article acoustic signature model;

signaling a first qualifying match when the captured potential use sound profile meets the stored absorbent article acoustic signature model;

interpreting the first qualifying match in view of at least one environmental input, the at least one environmental input being selected from the group consisting of: time of day, attitude recognition of a wearer of the absorbent article, and attitude recognition of a user of the absorbent article; and selectively generating a first output based on the first qualifying match and the at least one environmental input, the first output being recognizable by the user through visual, audible, or olfactory senses.

\* \* \* \* \*